United States Patent [19]

Obiaya

[11] 4,129,491

[45] Dec. 12, 1978

[54] OXYGEN CONCENTRATION ANALYZER

[76] Inventor: Joseph O. Obiaya, 4773 Walford, #13, Warrensville Heights, Ohio 44128

[21] Appl. No.: 845,048

[22] Filed: Oct. 25, 1977

[51] Int. Cl.² .......................................... G01N 27/46
[52] U.S. Cl. ............................................... 204/195 S
[58] Field of Search ............ 23/254 E, 255 E, 232 E; 73/23, 25, 26, 27 R; 204/1 S; 195 S

[56] References Cited
U.S. PATENT DOCUMENTS

| 3,546,086 | 12/1970 | Sayles | 204/195 S |
| 3,607,701 | 9/1971 | Wheeler | 204/195 S |
| 3,676,820 | 7/1972 | Taguchi | 23/254 E |
| 3,960,500 | 6/1976 | Ross et al. | 204/1 S |
| 4,013,943 | 3/1977 | Chou et al. | 23/254 E |

Primary Examiner—T. Tung
Attorney, Agent, or Firm—Watts, Hoffmann, Fisher & Heinke Co.

[57] ABSTRACT

An oxygen concentration analyzer is disclosed for measuring the concentration of oxygen within a sample gas. The analyzer includes an electrolyte reactor member for producing a voltage which can be correlated to oxygen concentration within the sample. Embedded within the reactor is a heater for maintaining the reactor member at an elevated temperature to insure proper lattice structure within the reactor electrolyte.

7 Claims, 7 Drawing Figures

OXYGEN CONCENTRATION ANALYZER

BACKGROUND AND SUMMARY OF THE INVENTION

This invention relates to an improved apparatus and technique for monitoring the oxygen concentration in a gas, e.g., in a combustible fuel environment.

Processes are known for testing the oxygen concentration of a sample gas. For example, U.S. Pat. No. 3,960,500 to Ross et al. discloses a zirconium oxide or zirconia analysis technique. To utilize this technique, it is necessary that the zirconia ($ZrO_2$) in the form of a solid electrolyte be doped with a magnesia, yttria, calcia, or other bivalient molecule. The presence of these doping materials in the zirconium oxide solid creates vacancies of oxygen (valence $-2$) ions in a way similar to a doping process in a semi-conductor material. The doping effect occurs at temperatures ranging from 300°-900° C., but for most effective ion concentration, a temperature of approximately 815° C. (1500° F.) insure a stable and efficient crystal lattice structure.

The zirconia is coated on both sides with a platinum electrode which serves as an electrical contact for conducting electrical current between the solid electrolyte and an external circuit. On one electrode oxygen molecules of a reference gas are reduced by combining them with electrons to provide oxygen ions. On the other electrode oxygen ions from the zirconium yield up their electrons to form new oxygen atoms. The former reaction is known as the cathodic reaction and the latter known as the anodic reaction. These two reactions occurring at the cathode and anode of the detector create a current flow which is equivalent to a voltage difference across the element. By utilizing the well-known Nernst equation and observing the voltage difference created by the half cell reactions it is possible to determine the oxygen concentration of a sample gas.

The Nernst equation is of the form;

$$E=(RT/nF) \ln (P_r/P_s),$$

where R is equal to the universal gas constant, F is equal to Faradays' number, T is equal to absolute temperature, $P_r$ and $P_s$ are the oxygen partial pressures of the reference and sample gases respectively, and n is the number of electrons transferred in the half cell reaction. Since one knows the partial pressure due to the reference gas and also knows the other elements of the equation, it is possible by determining the voltage difference across the electrodes, to determine the partial pressures of the sample gas and thereby determine the oxygen concentration of the sample.

In the prior art (see the Ross patent) the temperature rise required for proper crystal lattice structure was provided by an external furnace. The external furnace resulted in a number of disadvantages including the following: (a) the furnace presented an additional cost to the total system apparatus cost; (b) the furnace was bulky and cumbersome to work with; (c) the oxygen analyzer was not maneuverable and could not be placed directly into the sample gas; (d) the time required to reach the operating temperature of the sample analyzer was long, (approximately 15 minutes); and, (e) the temperature distribution of the apparatus was uneven (it was hotter on the top than on the bottom).

The present invention eliminates the problems of the prior art by directly embedding within the crystal lattice structure of the zirconium oxide a resistance heater element to obtain the proper operating temperature. The heater element comprises a metallic grid structure upon which the zirconium oxide can be molded or coated in such a manner that the heater element in no way disrupts the crystal lattice structure of the sensor. The heater element is attached to a standard source of voltage and in no way adds to system design complexity since it is already necessary that electric connections enter the system to monitor the voltage differences and thereby observe concentration.

The technique of directly embedding the heater in the zirconium oxide results in a number of improvements over the prior technique. The cost of an embedded heater element and the process of sensor fabrication is much less than the cost of providing heat by furnace radiation.

The heater element is in direct contact with the sensor, consequently the size of the apparatus is greatly reduced thereby allowing the utilization of a compact insulator guard in the immediate region of the sensor to further insure ambient temperature is maintained at a relatively constant value.

Because the heater element meshes in intimate contact with the sensor crystal structure, the temperature rise can be attained much quicker and uniform temperature distribution is easier to achieve.

The input power necessary to provide the energy to heat the apparatus is reduced because of the direct physical contact between the heater and the sensor.

Finally, the heater element provides a rugged frame for sensor fabrication thereby improving the durability of this sensor.

The above and other features and advantages of the invention will become more apparent as the invention becomes better understood from the detailed description that follows, when considered in connection with the accompanying drawings.

DETAILED DESCRIPTION

Figure 1:
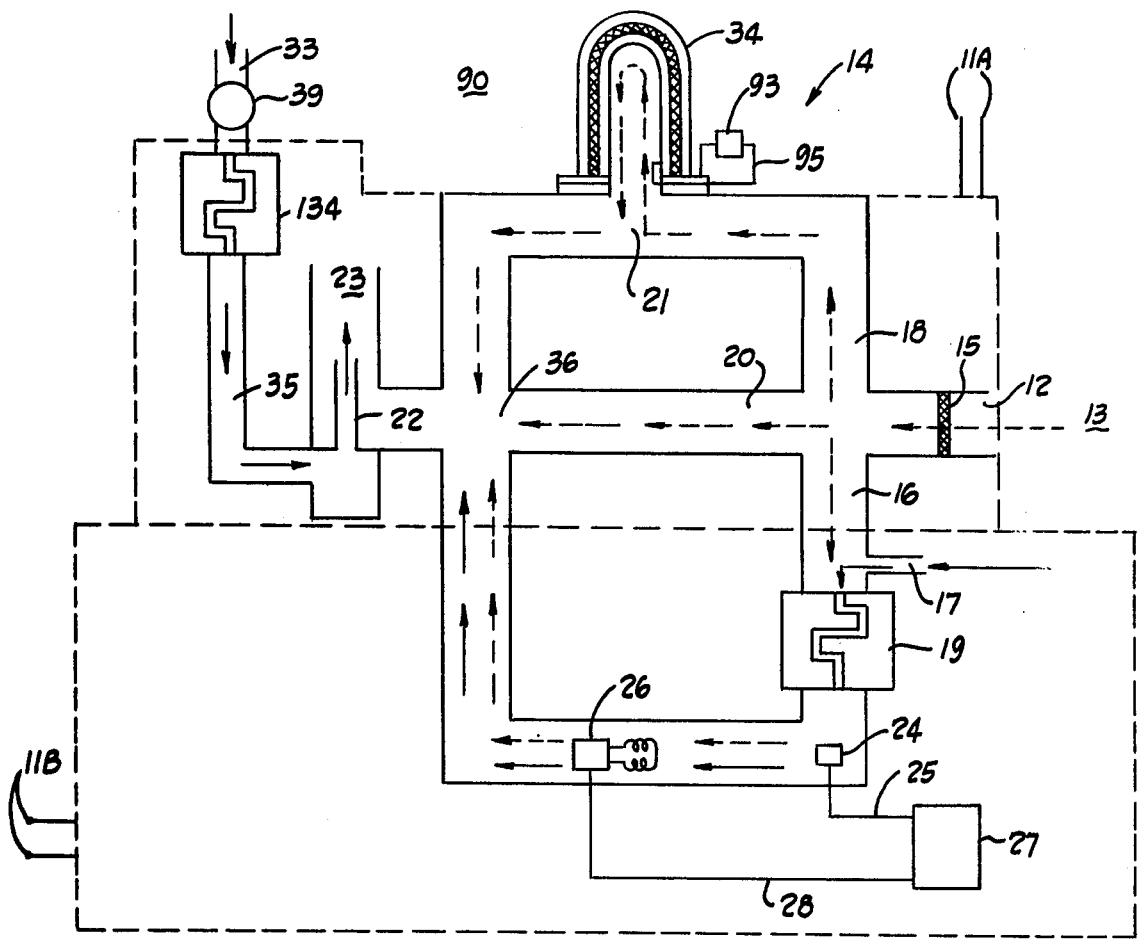
FIG. 1 is a schematic diagram of an oxygen concentration and combustible element concentration analyzing system embodying the present invention.

FIG. 1 presents a general schematic diagram of an oxygen concentration and combustible concentration analyzer comprising an inlet 12 for obtaining a sample of gas from a furnace or other sampling area 13, a conduit system 14 which divides into three portions 16, 18, and 20, and an outlet port 23 into which the three portions merge. Fluid flow within the conduit system 14 is maintained by means of an aspirator or eductor 22 located adjacent the outlet port. This configuration allows the gas to flow through the respective conduit portions, be analyzed by analyzers 26, 34 within the respective portions 16, 18, and be recombined and emitted from the outlet port 23.

The gaseous portion entering the conduit portion 16 will be tested for its combustible element content. It is combined with atmospheric air at an air inlet 17 in the conduit portion 16 and the combined flow then enters a heating labyrinth 19 which transfers ambient heat to the flow. After being heated in the labyrinth to a temperature of approximately 400° F., the gases comprising this portion of the sample are emitted from the heating labyrinth 19 and pass a pressure transmitter 24 which helps maintain proper calibration of the analyzer 26. After leaving the general area of the pressure sensor, the part of the sample passing through conduit portion 16 is tested by the combustible concentration analyzer 26 and is then recombined with the other portions of the gaseous sample.

A second portion of the gas sample to be analyzed by this system enters conduit portion 18 and travels along that conduit portion until it reaches an area 21 where the oxygen concentration analyzer 34 is located. A part of that sample gas enters the oxygen concentration analyzer 34 and travels along a generally U-shaped path until it again joins conduit portion 18. While within this confined area, a portion of oxygen within the gaseous sample interacts with the analyzer to produce an electrical output indicative of the oxygen concentration. The second sample portion then continues to travel along conduit portion 18 until it is reunited with the other gaseous elements.

The third conduit portion 20 serves to carry a third portion of the sample gas to the juncture 36 where the flows are recombined. This conduit facilitates gas flow and eliminates undesirable pressure variations within the system.

After reuniting at the juncture 36, the gases are swept from the system by the aspirator 22. Since the details of the aspirator are not part of this invention, it has been presented in the schematic form and may be one of a number of commercially available devices to produce the desired result. After analysis has been completed the sample is returned to the original source.

A final conduit 33 enters the system 14 to provide a source of compressed air to the aspirator 22. The compressed air passes through a pressure regulator 39 to maintain constant pressure in conduit 35 thereby insuring uniform aspirator operation. Uniform aspirator functioning results in uniform sample flow within the system 14, which is necessary for proper sensor calibration. The air is heated within a labyrinth heater 134 and passes through conduit 35 to the aspirator 22. If unheated compressed air is used in conduit 35 moisture condenses at the outlet port 23. Such condensation attracts dirt and dust particles which may clog the outlet port and interrupt sample flow through the system.

The entire conduit system 14 is heated to a temperature of 400° F. by block heater elements 11A and 11B. The precise mechanism for heating the system 14 to this level is not critical and can be accomplished in any commercially reasonable manner.

The labyrinth 19 of the combustible element analyzing portion of the system to transfer heat to the sample gas after it has been combined with a quantity of air at atmosphere pressure introduced through the inlet 17. In a preferred construction the labyrinth is either cast or machined to form an integral part of the combustible sample conduit path 16. The attainment of a 400° F. temperature of the gas is crucial in producing a catalytic reaction on the individual sensors of the combustibles analyzer, and since the sensor response is dependent upon the sample temperature, a reliable means of heating the sample fluid to a predetermined temperature within the system is a necessity. By including the labyrinth as a direct part of the combustible sample flow path, a reliable constant temperature of the sample can be assured by the ambient temperature of the labyrinth, which will facilitate calibrating the system. Passage of the sample through the labyrinth is an effective way to obtain final temperature of 400° F. After leaving the labyrinth 19 the sample passes the pressure sensor 24 and enters the region of the combustible concentration analyzer 26.

Figure 2:
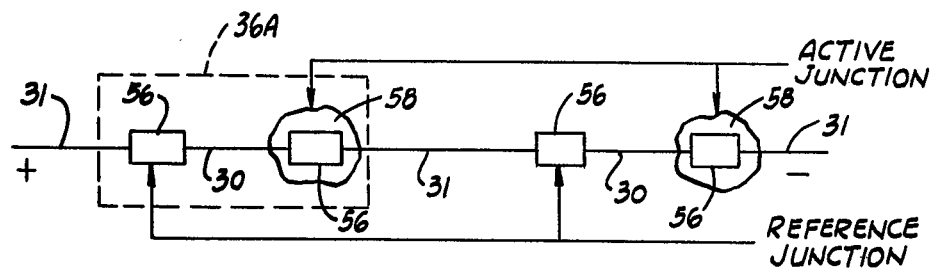
FIG. 2 is a schematic diagram of a number of series connected thermocouples for a combusible element analyzer.

As seen schematically in FIG. 2, the combustible concentration analyzer 26 comprises a number of series-connected thermo-couples 36A sensitive to temperature changes at their metallic junctions. This connection of thermo-couples forms a matrix arrangement (thermopile) whose shape can be varied. Each of the thermo-couples comprises a chromel element 30 and an alumel element 31 which are joined at junctions 56. While chromel and alumel have been chosen in the preferred embodiment of the invention other dissimilar metals can be chosen to form the thermo-couple. For example a segment of platinum could be joined to a segment of 90% platinum and 10% rhodium to produce the required effect. Also other percentages of the platinum-rhodium alloy could be chosen. At a chromel-alumel junction any temperature variation above the ambient temperature of the rest of the configuration will produce a current flow within the arrangement. To transform the chromel-alumel series connected thermo-couples into a combustible element analyzer, a platinum element 58 (see FIG. 2) which is a paste is coated upon alternate junctions. The platinum coated junction is referred to as an active or catalytic junction and the non-coated junction as a reference or non-catalytic junction.

The platinum element 58 induces an exothermic reaction within the combustible concentration analyzer. Platinum was chosen for two reasons; (a) the platinum will effectively catalyse a reaction between oxygen and a combustible element within the system when a high enough ambient temperature is maintained, and (b) the platinum catalyst element effectively withstands any degradation due to the presence of unwanted foreign elements which enter the system with the sample gas. For example, the platinum catalyst element is especially resistent to the poisonous effects of sulphur dioxide ($SO_2$) at elevated temperature above 800° F. With the platinum catalyst element in place the chromel-alumel pairs in combination with their crimping elements and the catalyst complete the construction of the matrix arrangement. While the platinum paste is preferred due to its operating characteristics in an environment with high sulfur dioxide concentrations, other substances such as a palladium paste can be used to catalyse the reaction.

Figure 3:
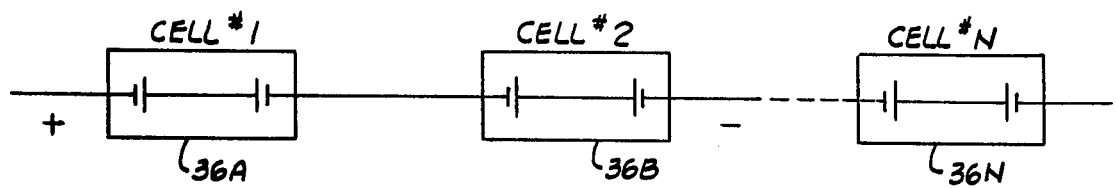
FIG. 3 is a diagram showing the functional equivalence between series connected thermocouples and series connected batteries.

As seen in FIG. 3, the combination of the series connected thermo-couples plus the catalytically induced exothermic reactions produces an effect similar to a series connection of batteries. Every active-reference junction pair can be thought of as an individual cell 36A, 36B and 36N which produces a voltage difference within the series connected system. With reference to FIGS. 2 and 3, the configuration of the chromel-alumel pairs depicted indicates a voltage increase from right to left. Each succeeding active-reference pair produces a voltage difference due to the exothermic reaction occuring at the active junction. The total system output from this configuration can be found by summing the individual voltage differences on the thermo-couple connections. As seen in FIG. 3 this would be equivalent to N times the voltage difference from one active-reference pair.

Reversing the order of the chromel 30 alumel 31 pairs in the sensor causes the electrical polarity of the system of reverse. If in FIG. 2 the chromel elements 30 were changed to alumel 31 and vice versa the voltage would increase from left to right. The sequence depicted in FIG. 3 is preferable, however, due to improved signal to noise ratio of that configuration.

Figure 4:
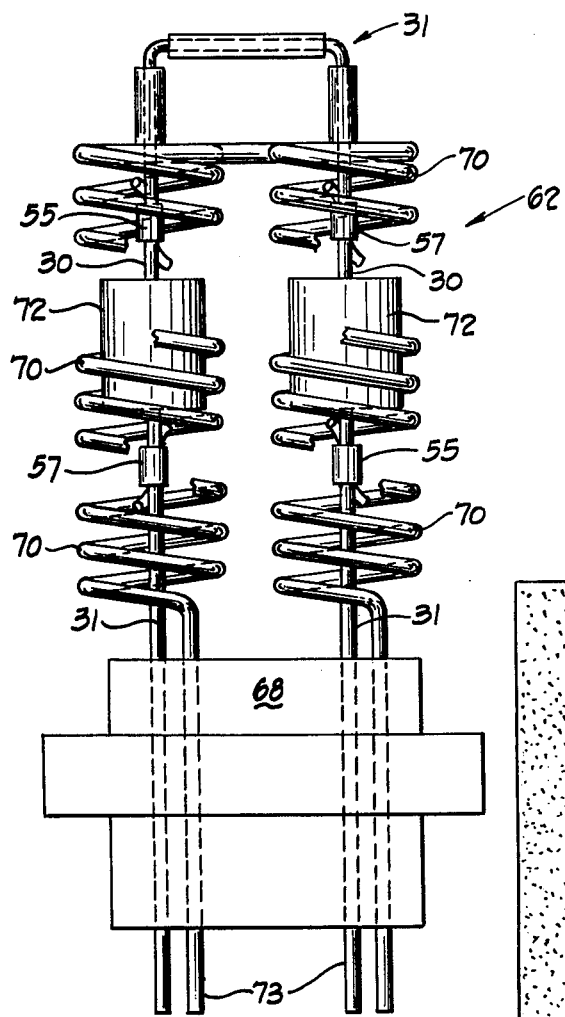
FIG. 4 depicts a functional combustible element analyzer formed by crimping together discreet thermocouple elements.

One arrangement of the thermo-couple configured combustible analyzer is shown in FIG. 4. This analyzer comprises a base 68 and a series of connected thermo-couples 62 arranged in a U-shaped configuration. Mechanically, links of alumel and chromel are held together by a series of crimp materials 55 and 57 placed around the chromel-alumel elements to form a junction. In the present arrangement the crimp for a reference junction 55 is made of silver and the crimp for an active junction 57 made of platinum.

In the system shown in FIG. 4, a platinum catalyst material 58 (shown only in FIG. 2) is applied to alternate crimp junctions 57 within the system. In order to raise the ambient temperature of the thermo-couples to a range of approximately 800° F. (i.e., 400° F. higher than the sample entering the combustible sensor) a series of heating coils 70 are arranged coaxially with the thermo couple series connections. These heater coils are connected to a source of voltage and due to joule heating cause a rise in the ambient temperature surrounding the junctions. The 800° F. operating temperature is desirable primarily to eliminate $SO_2$ poisoning of the catalyst element 58. Since the heating elements are connected to a source of electrical energy, it is necessary that they be insulated electrically from the thermopile conduction matrix. For this reason a bead-like element 72 is imposed between the heater coils and the thermo-couple junctions. This element can be of any suitable material which will conduct heat while insulating the elements from electrical contact. In the preferred embodiment this bead insulation material is mullite and is bound to the heating coils 70 by a suitable contact cement.

The electrical leads to both the thermo-couple matrix and the heater coils 70 pass through the base 68 to a standard electrical pin connector 73 to achieve electrical insulation of the output signal of the combustion concentration analyzer from the heat coil.

Figure 6:
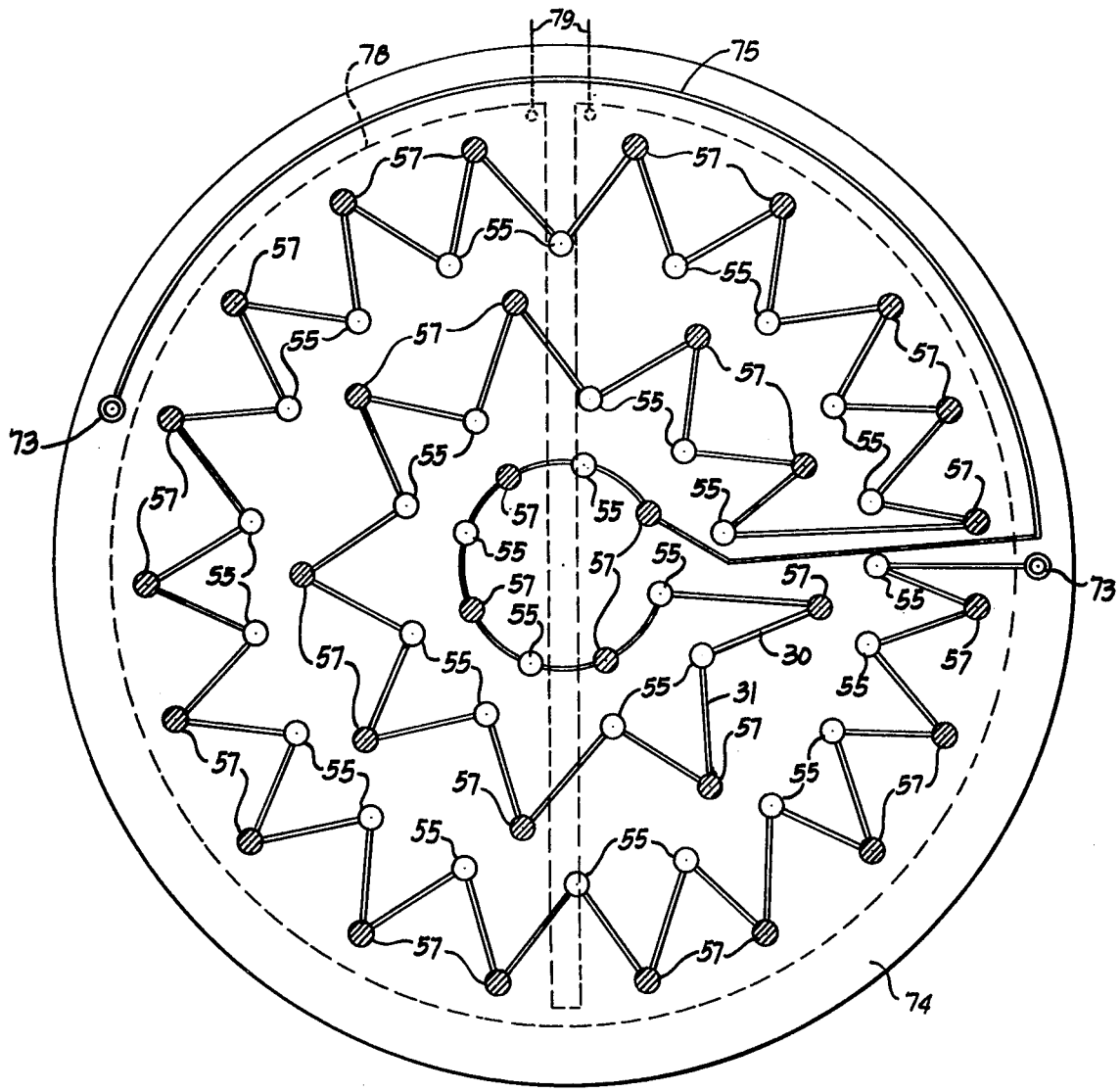
FIG. 6 is a plan view of a combustible element analyzer constructed using a sputter-etch technique which provides improved sensitivity readings.

A second version of the combustible element analyzer is shown in FIG. 6. This apparatus works on the same principal as that of FIG. 4 but posesses certain attributes which are superior. As seen in FIG. 6, a number of chromel 30 and alumel 31 pairs are sputter-etched in the form of a thermopile matrix. The alternating active junctions 57 of these pairs are coated with a catalyst material 58 which produces the exothermic reaction in a similar manner to the prior noted device. The difference between the two is the physical construction and fabrication technique involved. The analyzer of FIG. 6 is comprised of layers coated upon a substrate material 74. Through the use of a masking technique similar to those used in integrated circuit fabrication, the chromel-alumel and catalyst elements are successively sputter-etched onto the substrate material at desired locations to form an operating thermopile matrix of thermo-couples. The precise order and configuration of the chromel-alumel and catalyst etching are not critical to system performance. The electrical interconnection circuit 75 is also sputtered onto the substrate material 74 in a pattern to connect the thermo-couple matrix to the connections 73. As in the arrangement of FIG. 4, it is necessary to again raise the temperature of the ambient conditions surrounding the chromel-alumel pairs to approximately 800° F. To attain this temperature, a resistance heating circuit 78 shown in phantom comprising a resistive element has been sputter-etched upon the substrate on the surface opposite to the combustible analysis matrix. In this way electrical insulation is readily obtained between the thermopile and contacts 79 to the heating circuit and as long as the substrate material is a good conductor of heat the ambient temperature surrounding the junctions 55 and 57 necessary for preventing $SO_2$ poisoning effect is achieved.

By using the masking fabrication process to produce the construction of FIG. 6, it is possible to achieve combustible concentration analyzer uniformity and increased production capabilities. It should also be noted that the increased number of alumel-chromel junctions increases the sensitivity to the point that even low levels of combustible concentration produce large enough signals for analysis.

The two combustible concentration analysis devices of FIGS. 4 and 6 produce a voltage at their pin connections 73 which is directly proportional to the concentration of the combustible in the sample gaseous fluid. This relationship follows from the functional correlation between heat given off and combustible concentration present at the active junctions. The voltage from the pin connections 73 of the matrix is then calibrated to yield the combustible element concentration. This calibration is done by utilizing a gas of known concentration to obtain reference readings upon a suitable volt meter 27. (see FIG. 1). These reference readings and the proportional relation between voltage and concentration allows interpolation to other concentration values. Since the particular reading device utilized is variable and not an element of the present invention, details of this calibration technique have been omitted.

As seen in FIG. 1, the design of the present system includes a filter or guard 15 which helps eliminate foreign elements such as dirt and unwanted particles which could adversely affect the operation of the total system. For industrial application where the gas carries particulate water or dirt, it has been found that the filter tends to clog with particles and a reduced flow rate within the conduit system 14 results due to reduced pressure differences along the system. If, for example, dirt and other elements within the sample environment cause the filter element to clog, the pressure variations from one portion of the conduit to the other vary to a lesser degree. This reduced pressure drop results in a reduced flow rate of the combustible sample past the combustible sample element analyzer 26 and adversely affects the system calibration. If, for example, the amount of combustible passing by the analyzer 26 per unit time is reduced, fewer reactions can take place along the matrix thereby indicating a lower combustion concentration.

This happens when, in fact, the combustible concentration has remained unchanged, and only the flow rate within the conduit 16 has been altered. To take into account the change in flow rate, a pressure sensor 24 has been introduced within the combustible analysis conduit 16.

The pressure transmitter 24 is one of a number of commercially available devices which sense changes in pressure. Attached to the pressure transmitter is an electrical interconnect 25 which transmits the output from the device 24 to the voltmeter 27. When the output from the pressure transmitter 24 is added to the combustible concentration analyzer output 28, a reading is produced that compensates for reduced flow rate due to the environment in which this system must operate. By way of example, if one uses a pressure transmitter which produces a voltage reading directly proportional to the pressure drop, one can add the output from this device interconnect 25 to the combustible concentration analyzer output interconnect 28 to produce a signal whose voltage is independent of flow rate within the conduit. Thus it is apparent that the system can be calibrated using one flow rate, but by utilization of a pressure sensor, will be accurate for all flow rates within the sensing capabilities of the combustion analyzer.

The upper conduit portion 18 in FIG. 1 provides a channel for the sample gas to be routed for oxygen concentration analysis. The sample gas flows through the upper conduit to the oxygen sensor 34. The oxygen sensor comprises a U-shaped or closed-end tubular member which forms a chamber 85 (see FIG. 5) within which the sample gas is allowed to flow. A base 80 serves as a support mount for an oxygen sensor heater element 86 that is in the form of a grid and mesh construction. Interwoven and layered upon opposite sides of the heater element 86 is a crystal-type structure of zirconium oxide 82.

Figure 7:
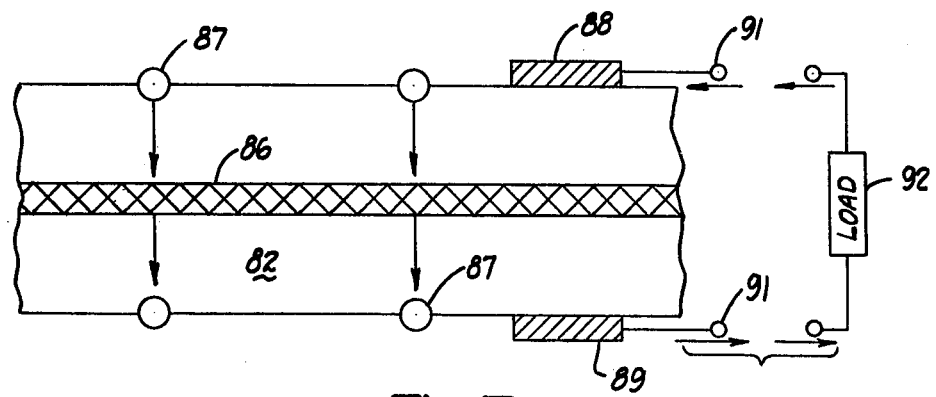
FIG. 7 is a schematic diagram showing oxygen ion migration within the oxygen concentration analyzer.

Functionally the oxygen concentration sensor operates using a voltaic reaction which involves the transfer of chemical energy into electrical energy. The zirconium oxide 82 is doped with a bivalent molecule such as magnezia, yttria, calcia to produce vacancies of minus 2 valence oxygen ions 87 (FIG. 7) within the crystal structure of the zirconium oxide.

By the use of platinum electrodes 88 and 89 (see FIG. 7) on opposite zirconium oxide surfaces one can induce a chemical reaction within the zirconium oxide (assuming proper ion concentration due to doping). The reaction at the cathode follows the relation:

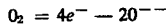

and at the anode:

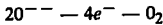

In the present invention the anode electrode 89 is in contact with the sample gas within the chamber 85 and the cathode electrode 88 is in contact with the surrounding atmosphere 90 which acts as a source of known oxygen concentration. If an external load circuit 92 is attached to the electrodes, the combination of the two half cell reactions at the cathode and anode cause oxygen ion migration and therefore a current to flow within the circuit.

The voltage created by this reaction is given by the Nernst equation:

$$E = (RT/nF) \ln P_r/P_s$$

where
R = Universal Gas Content
F = Faraday's Number
T = Absolute Temperature
$P_r$ = Oxygen Partial Pressure of reference gas.
$P_s$ = Oxygen Partial Pressure of sample gas.
n = number of electrons transferred in half cell equation.

Since the oxygen concentration of the surrounding atmosphere 90 is known, its partial pressure can be determined if atmospheric pressure is known. The voltage difference at a pair of electrode connections 91 can be measured by use of a suitable voltmeter 93 substituted in place of the load circuit 92. By combining this information with the other components of the Nernst equation, oxygen partial pressure in the sample can be calculated and through knowledge of the sample pressure the percent oxygen concentration calculated. Alternatively, knowledge that the voltage difference at the electrodes 88 and 89 is proportional to $\ln (1/P_s)$ enables the user to calibrate a suitable voltmeter by using a sample of known oxygen concentration.

Figure 5:
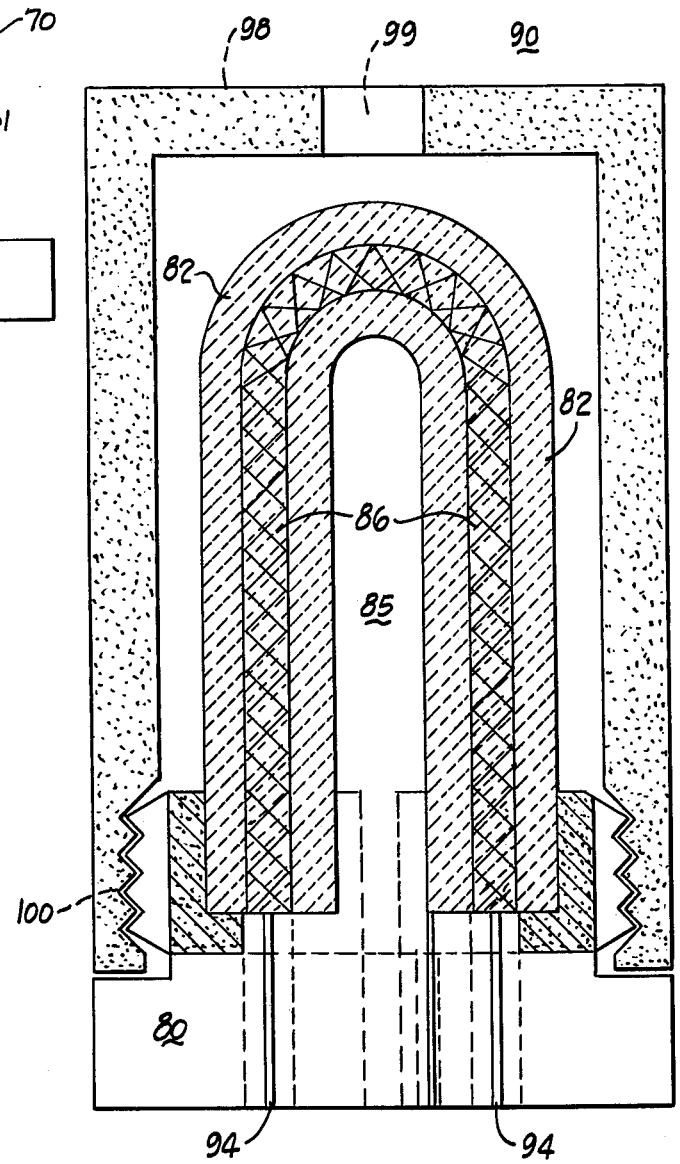
FIG. 5 is a sectional view of an improved oxygen concentration analyzer.

The voltaic reaction occuring in the oxygen sensor is sensitive to temperature conditions. The most suitable lattice structure and ion concentration within the zirconium oxide occurs at approximately 1500° F. The present invention utilizes a heater element 86 directly embeded within the zirconium oxide 82. The zirconium oxide is coated to the heater and extends around and through the mesh structure as seen in FIG. 5. This configuration facilitates ion flow within the doped zirconium oxide directly through the heater element 86. The heater element therefore gives structure to the zirconium oxide element without disrupting its well-defined crystal lattice structure. The element 86 is energized by power connections 94 and may be either A.C. or D.C. operated. Care must, of course, be taken to insure that the power connections 94 to the heater 86 are electrically insulated from the conductors 95 leading from the oxygen sensing electrodes 88 and 89 to the voltmeter 93. Surrounding the oxygen analyzer 34 is a insulation guard 98 as seen in FIG. 5. This guard screws onto the base 80 by means of a threaded coupling 100 and includes an opening 99 for receiving air from the surrounding atmosphere 90. The guard insures against excessive heat loss and therefore is made of appropriate heat insulating material.

After the oxygen concentration sample has been tested it returns to the oxygen conduit 18 and recombines with the samples from the other conduits 16 and 20 before being ejected out the outlet 23.

While the present invention has been described with particularity, it should be understood that various modifications and alterations may be made therein without departing from the spirit and scope of the invention set forth in the appended claims.

What is claimed is:

1. An oxygen concentration analyzer comprising:
   (a) a material comprised of zirconium oxide doped with bivalent molecules the presence of which within the material creates oxygen ion vacancies;
   (b) a heater embedded with said material for heating said material; said heater configured in the form of a structure with meshes and capable of radiating heat to said material while allowing oxygen ions in said material to migrate through meshes of said structure;

(c) means for structurally supporting said heater;

(d) a first conductive electrode on one area of said material to facilitate the reduction of oxygen molecules in a first gas;

(e) a second conductive electrode on a second area of said material to facilitate the oxidation of gas ions within said material, said second conductive electrode being located for exposure to a second gas; and (f) means for electrically connecting said first and second electrodes to means for correlating voltage difference between said electrodes with oxygen concentration within said first or second gas.

2. The oxygen concentration analyzer of claim 1 wherein said mesh structure comprises electrically conductive elements and wherein said analyzer further comprises means for electrically connecting said mesh to a source of electrical power.

3. The oxygen concentration analyzer of claim 2 wherein said mesh structure provides additional support for said material and establishes the shape thereof.

4. The oxygen concentration analyzer of claim 3 wherein said shape is a general U-shaped tubular configuration with the first conductive electrode located on the concave portion of said U-shaped configuration and the second conductive electrode located on the convex portion of said U-shaped configuration.

5. The oxygen concentration analyzer of claim 4 wherein the first gas is the sample whose oxygen concentration is to be analyzed, the second gas is a sample whose oxygen concentration is known, and wherein said first and second conductive electrodes are comprised of platinum.

6. An oxygen concentration analyzer for measuring the concentration of oxygen within a sample gas comprising a reactor member and a base for mounting said member; said member including a solid electrolyte with oxygen ion vacancies providing paths for oxygen ion migration within said electrolyte, a mesh structure embedded within said electrolyte for heating said electrolyte and providing structural support to said electrolyte, a first and second conductive electrode for inducing a voltage reaction within the sample, and means for connecting said first and second electrodes to external voltage measuring means for measuring voltage differences between said electrodes.

7. The analyzer of claim 6 wherein said member defines a flow confining path for a sample gas, the first said electrode being isolated from the flow confining path and the second said electrode being along at least a part of said path, and said heating means being between said first and second electrodes.

* * * * *